United States Patent
Wang et al.

(10) Patent No.: US 11,746,134 B2
(45) Date of Patent: Sep. 5, 2023

(54) HUMAN FGF21 MUTANT WITH IMPROVED EFFECTIVENESS AND STABILITY AND PHARMACEUTICAL COMPOSITION THEREOF

(71) Applicant: Heifei Zhongke Longwood Biotechnology Co., Ltd., Hefei (CN)

(72) Inventors: Junfeng Wang, Hefei (CN); Hongxin Zhao, Hefei (CN); Lei Zhu, Hefei (CN)

(73) Assignee: Heifei Zhongke Longwood Biotechnology Co., Ltd., Hefei (CN)

( * ) Notice: Subject to any disclaimer, the term of this patent is extended or adjusted under 35 U.S.C. 154(b) by 207 days.

(21) Appl. No.: 16/608,706

(22) PCT Filed: Apr. 11, 2018

(86) PCT No.: PCT/CN2018/082669
§ 371 (c)(1),
(2) Date: Jan. 14, 2021

(87) PCT Pub. No.: WO2018/196616
PCT Pub. Date: Nov. 1, 2018

(65) Prior Publication Data
US 2021/0163560 A1    Jun. 3, 2021

(30) Foreign Application Priority Data
Apr. 28, 2017    (CN) .......................... 201710302732.X

(51) Int. Cl.
*A61K 38/18* (2006.01)
*C07K 14/50* (2006.01)
*A61K 38/00* (2006.01)

(52) U.S. Cl.
CPC .......... *C07K 14/50* (2013.01); *A61K 38/1825* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,188,040 B2 | 5/2012 | Belouski et al. | |
| 8,410,051 B2 * | 4/2013 | Belouski ............ | A61K 38/1825 435/243 |
| 8,618,053 B2 | 12/2013 | Belouski et al. | |
| 8,795,985 B2 | 8/2014 | Belouski et al. | |
| 8,835,385 B2 | 9/2014 | Belouski et al. | |
| 10,583,174 B2 * | 3/2020 | Göbel et al. ........... | A61K 38/39 |
| 2010/0285131 A1 | 11/2010 | Belouski et al. | |
| 2012/0177646 A1 | 7/2012 | Belouski et al. | |
| 2012/0178685 A1 | 7/2012 | Belouski et al. | |
| 2012/0213779 A1 | 8/2012 | Belouski et al. | |
| 2014/0213512 A1 | 7/2014 | Ellison et al. | |

FOREIGN PATENT DOCUMENTS

| | | |
|---|---|---|
| CN | 102655877 A | 9/2012 |
| CN | 103923207 A | 7/2014 |
| CN | 107056925 A | 8/2017 |
| JP | 2014526441 A | 10/2014 |
| JP | 2015165801 A | 9/2015 |
| WO | WO-2011047267 A1 | 4/2011 |
| WO | WO-2013033452 A3 | 4/2013 |

OTHER PUBLICATIONS

Hecht, Randy, et al., "Rationale-based engineering of a potent long-acting FGF21 analog for the treatment of type 2 diabetes", PloS one 7.11, (2012), e49345.

Song, Lintao, et al., "A solid-phase PEGylation strategy for protein therapeutics using a potent FGF21 analog", Biomaterials 35.19, (2014), 5206-5215.

Stanislaus, Shanaka, et al., "A novel Fc-FGF21 with improved resistance to proteolysis, increased affinity toward ß-klotho, and enhanced efficacy in mice and cynomolgus monkeys", Endocrinology 158.5, (2017), 1314-1327.

Oda, Hiroyo, "Japanese Application Serial No. 2020-509145, Office Action dated Mar. 23, 2021", w English Translation, (Mar. 23, 2021), 10 pgs.

* cited by examiner

Primary Examiner — Christine J Saoud
(74) Attorney, Agent, or Firm — Schwegman Lundberg & Woessner, P.A.

(57) ABSTRACT

The present disclosure relates to a human FGF21 mutant with improved effectiveness and stability, preparation method and pharmaceutical composition comprising the mutant, and a use thereof, and specifically relates to a human fibroblast growth factor 21 (FGF21) mutant, a gene encoding the same, and a method for preparing the mutant and a method of using the mutant for treating type 2 diabetes, obesity, dyslipidemia, or metabolic disorders.

2 Claims, 6 Drawing Sheets
Specification includes a Sequence Listing.

SEQUENCE LISTING

```
<160> NUMBER OF SEQ ID NOS: 21

<210> SEQ ID NO 1
<211> LENGTH: 181
<212> TYPE: PRT
<213> ORGANISM: Homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 543
<212> TYPE: DNA
<213> ORGANISM: Homo sapiens

<400> SEQUENCE: 2 cacccatcc ctgactccag tcctctcctg caattcgggg gccaagtccg gcagcggtac    60
```

```
ctctacacag atgatgccca gcagacagaa gcccacctgg agatcaggga ggatgggacg    120 gtgggggcg ctgctgacca gagccccgaa agtctcctgc agctgaaagc cttgaagccg     180
ggagttattc aaatcttggg agtcaagaca tccaggttcc tgtgccagcg ccagatggg     240 gccctgtatg gatcgctcca ctttgaccct gaggcctgca gcttccggga gctgcttctt    300
gaggacggat acaatgttta ccagtccgaa gcccacggcc tcccgctgca cctgccaggg    360
aacaagtccc cacaccggga ccctgcaccc cgaggaccag ctcgcttcct gccactacca    420
ggcctgcccc ccgcactccc ggagccaccc ggaatcctgg ccccccagcc cccgatgtg     480 ggctcctcgg accctctgag catggtggga ccttcccagg ccgaagccc cagctacgct     540 tcc                                                                 543
```

<210> SEQ ID NO 3
<211> LENGTH: 546
<212> TYPE: DNA
<213> ORGANISM: Artificial Sequence
<220> FEATURE:
<223> OTHER INFORMATION: A synthetic sequence

<400> SEQUENCE: 3

```
cacccccatcc ctgactccag tcctctcctg caattcgggg gccaagtccg gcagcggtac    60
ctctacacag atgatgccca gcagacagaa gcttgccacc tggagatcag ggaggatggg    120
acggtggggt cgctgctga ccagagcccc gaaagtctcc tgcagctgaa agccttgaag     180
ccgggagtta ttcaaatctt gggagtcaag acatccaggt tcctgtgcca gcggccagat    240
ggggccctgt atgatcgct ccactttgac cctgaggcct gcagcttccg ggagctgctt    300
cttgaggacg gatacaatgt ttaccagtcc gaagcccacg gcctcccgct gcacctgcca    360
gggaacaagt cccacaccg gaccctgca ccccgaggac cagctcgctt cctgccacta    420
ccaggcctgc ccccgcact cccggagcca cccggaatcc tggcccccca gcccccgat    480 gtgggctcct cggaccctct gagcatggtg ggaggttccc agggccgaag ccccagctac    540
gcttcc                                                              546
```

<210> SEQ ID NO 4
<211> LENGTH: 182
<212> TYPE: PRT
<213> ORGANISM: Artificial Sequence
<220> FEATURE:
<223> OTHER INFORMATION: A synthetic sequence

<400> SEQUENCE: 4

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala Cys
            20                  25                  30

His Leu Glu Ile Arg Glu Asp Gly Thr Val Gly Cys Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

```
His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg
                165                 170                 175

Ser Pro Ser Tyr Ala Ser
            180

<210> SEQ ID NO 5
<211> LENGTH: 546
<212> TYPE: DNA
<213> ORGANISM: Artificial Sequence
<220> FEATURE:
<223> OTHER INFORMATION: A synthetic sequence

<400> SEQUENCE: 5
caccccatcc ctgactccag tcctctcctg caattcgggg gccaagtccg gcagcggtac     60
ctctacacat caggacctca tgggctctca agttgccacc tggagatcag ggaggatggg    120
acggtggggt gcgctgctga ccagagcccc gaaagtctcc tgcagctgaa agccttgaag    180
ccgggagtta ttcaaatctt gggagtcaag acatccaggt tcctgtgcca gcggccagat    240
ggggccctgt atggatcgct ccactttgac cctgaggcct gcagcttccg ggagctgctt    300
cttgaggacg gatacaatgt ttaccagtcc gaagcccacg gcctcccgct gcacctgcca    360
gggaacaagt ccccacaccg ggaccctgca ccccgaggac cagctcgctt cctgccacta    420
ccaggcctgc cccccgcact cccggagcca cccggaatcc tggcccccca gcccccgat    480 gtgggctcct cggaccctct gagcatggtg ggaggttccc agggccgaag ccccagctac    540
gcttcc                                                               546

<210> SEQ ID NO 6
<211> LENGTH: 182
<212> TYPE: PRT
<213> ORGANISM: Artificial Sequence
<220> FEATURE:
<223> OTHER INFORMATION: A synthetic sequence

<400> SEQUENCE: 6

His Pro Ile Pro Asp Ser Ser Pro Leu Leu Gln Phe Gly Gly Gln Val
1               5                   10                  15

Arg Gln Arg Tyr Leu Tyr Thr Ser Gly Pro His Gly Leu Ser Ser Cys
            20                  25                  30

His Leu Glu Ile Arg Glu Asp Gly Thr Val Gly Cys Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125
```

```
Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Gly Ser Gln Gly Arg
                165                 170                 175

Ser Pro Ser Tyr Ala Ser
                180

<210> SEQ ID NO 7
<211> LENGTH: 32
<212> TYPE: DNA
<213> ORGANISM: Artificial Sequence
<220> FEATURE:
<223> OTHER INFORMATION: A synthetic sequence

<400> SEQUENCE: 7
gggaattcca tatgcatcat catcatcatc ac                          32

<210> SEQ ID NO 8
<211> LENGTH: 24
<212> TYPE: DNA
<213> ORGANISM: Artificial Sequence
<220> FEATURE:
<223> OTHER INFORMATION: A synthetic sequence

<400> SEQUENCE: 8
ccgctcgagt caggaagcgt agct                                   24

<210> SEQ ID NO 9
<211> LENGTH: 38
<212> TYPE: DNA
<213> ORGANISM: Artificial Sequence
<220> FEATURE:
<223> OTHER INFORMATION: A synthetic sequence

<400> SEQUENCE: 9
cagagaacag attggtggtc accccatccc tgactcca                    38

<210> SEQ ID NO 10
<211> LENGTH: 38
<212> TYPE: DNA
<213> ORGANISM: Artificial Sequence
<220> FEATURE:
<223> OTHER INFORMATION: A synthetic sequence

<400> SEQUENCE: 10
tggagtcagg gatggggtga ccaccaatct gttctctg                    38

<210> SEQ ID NO 11
<211> LENGTH: 27
<212> TYPE: DNA
<213> ORGANISM: Artificial Sequence
<220> FEATURE:
<223> OTHER INFORMATION: A synthetic sequence

<400> SEQUENCE: 11
catggtggga ggttcccagg gccgaag                                27

<210> SEQ ID NO 12
<211> LENGTH: 27
<212> TYPE: DNA
<213> ORGANISM: Artificial Sequence
<220> FEATURE:
<223> OTHER INFORMATION: A synthetic sequence
```

<400> SEQUENCE: 12
cttcggccct gggaacctcc caccatg                                       27

<210> SEQ ID NO 13
<211> LENGTH: 27
<212> TYPE: DNA
<213> ORGANISM: Artificial Sequence
<220> FEATURE:
<223> OTHER INFORMATION: A synthetic sequence

<400> SEQUENCE: 13
gggacggtgg ggtgcgctgc tgaccag                                       27

<210> SEQ ID NO 14
<211> LENGTH: 27
<212> TYPE: DNA
<213> ORGANISM: Artificial Sequence
<220> FEATURE:
<223> OTHER INFORMATION: A synthetic sequence

<400> SEQUENCE: 14
ctggtcagca gcgcacccca ccgtccc                                       27

<210> SEQ ID NO 15
<211> LENGTH: 28
<212> TYPE: DNA
<213> ORGANISM: Artificial Sequence
<220> FEATURE:
<223> OTHER INFORMATION: A synthetic sequence

<400> SEQUENCE: 15
cagcagacag aagcttgcca cctggaga                                      28

<210> SEQ ID NO 16
<211> LENGTH: 28
<212> TYPE: DNA
<213> ORGANISM: Artificial Sequence
<220> FEATURE:
<223> OTHER INFORMATION: A synthetic sequence

<400> SEQUENCE: 16
tctccaggtg gcaagcttct gtctgctg                                      28

<210> SEQ ID NO 17
<211> LENGTH: 58
<212> TYPE: DNA
<213> ORGANISM: Artificial Sequence
<220> FEATURE:
<223> OTHER INFORMATION: A synthetic sequence

<400> SEQUENCE: 17
agcggtacct ctacacatca ggacctcatg ggctctcaag ttgccacctg gagatcag     58

<210> SEQ ID NO 18
<211> LENGTH: 58
<212> TYPE: DNA
<213> ORGANISM: Artificial Sequence
<220> FEATURE:
<223> OTHER INFORMATION: A synthetic sequence

<400> SEQUENCE: 18
ctgatctcca ggtggcaact tgagagccca tgaggtcctg atgtgtagag gtaccgct     58

<210> SEQ ID NO 19

```
<211> LENGTH: 8
<212> TYPE: PRT
<213> ORGANISM: Artificial Sequence
<220> FEATURE:
<223> OTHER INFORMATION: A synthetic sequence

<400> SEQUENCE: 19

Asp Asp Ala Gln Gln Thr Glu Ala
1               5

<210> SEQ ID NO 20
<211> LENGTH: 8
<212> TYPE: PRT
<213> ORGANISM: Artificial Sequence
<220> FEATURE:
<223> OTHER INFORMATION: A synthetic sequence

<400> SEQUENCE: 20

Ser Gly Pro His Gly Leu Ser Ser
1               5

<210> SEQ ID NO 21
<211> LENGTH: 8
<212> TYPE: PRT
<213> ORGANISM: Artificial Sequence
<220> FEATURE:
<223> OTHER INFORMATION: A synthetic sequence
<221> NAME/KEY: SITE
<222> LOCATION: 1
<223> OTHER INFORMATION: Xaa = Ser or Asp
<221> NAME/KEY: SITE
<222> LOCATION: 2
<223> OTHER INFORMATION: Xaa = Gly or Asp
<221> NAME/KEY: SITE
<222> LOCATION: 3
<223> OTHER INFORMATION: Xaa = Pro or Ala
<221> NAME/KEY: SITE
<222> LOCATION: 4
<223> OTHER INFORMATION: Xaa = Ala or Gln
<221> NAME/KEY: SITE
<222> LOCATION: 5
<223> OTHER INFORMATION: Xaa = Gly or Gln
<221> NAME/KEY: SITE
<222> LOCATION: (6)...(6)
<223> OTHER INFORMATION: Xaa = Leu or Tyr
<221> NAME/KEY: SITE
<222> LOCATION: (7)...(7)
<223> OTHER INFORMATION: Xaa = Ser or His
<221> NAME/KEY: SITE
<222> LOCATION: (8)...(8)
<223> OTHER INFORMATION: Xaa = Ser or Ala

<400> SEQUENCE: 21

Xaa Xaa Xaa Xaa Xaa Xaa Xaa Xaa
1               5
```

US 11,746,134 B2

HUMAN FGF21 MUTANT WITH IMPROVED EFFECTIVENESS AND STABILITY AND PHARMACEUTICAL COMPOSITION THEREOF

This application is a U.S. National Stage Filing under 35 U.S.C. 371 from International Application No. PCT/CN2018/082669, filed on Apr. 11, 2018, and published as WO 2018/196616 A1 on Jan. 11, 2018, which claims the benefit of priority to Chinese Patent Application No. 201710302732.X filed on Apr. 28, 2017, each of which is incorporated by reference herein in its entirety.

TECHNICAL FIELD

The disclosure belongs to the field of protein engineering. In particular, it relates to a human fibroblast growth factor 21 (FGF21) mutant, a gene encoding the same, and a preparation method of the mutant and a method of using the mutant for treating type 2 diabetes, obesity, dyslipidemia or metabolic disorders.

BACKGROUND

FGF21 is a secreted protein of the fibroblast growth factor (FGF) 19 subfamily which includes FGF19, FGF21, and FGF23 (Itoh et al., 2004, Trend Genet. 20:563-69). FGF21 is an atypical FGF which is independent of heparin and functions in metabolism of glucose, lipids and energy. It promotes glucose uptake in adipocytes by up-regulating GLUT1 expression, the mechanism of which is different from that of insulin. In rodents, monkeys and human with diabetes, FGF21 reduces the fasting serum concentration of glucose was well as the fasting serum concentrations of triglycerides, insulin and glucagon. Furthermore, administration of FGF21 results in a dose-dependent loss of cumulative body weight in a rodent diet-inducing obese model. Experimental studies have supported pharmacological administration of FGF21 for the treatment of diabetes, obesity, dyslipidemia, and metabolic syndrome.

However, because human FGF21 is easily degraded, administered at a high dosage, and has poor stability and efficacy, it is necessary to modify wild type FGF21 to improve its effectiveness and stability, thereby reducing the dose administered to patients.

SUMMARY

In order to solve the above problems, the present disclosure provides an alternative human FGF21 mutant, a gene encoding the same, and a preparation method and use of the mutant.

In particular, in one aspect, the disclosure provides a human FGF21 mutant having the following amino acid changes based on the amino acid sequence of the wild-type human FGF21 protein:

1) one Cys inserted at a position between Ala at position 31 and His at position 32 of the amino acid sequence of wild type human FGF21 protein, and Cys substitution(s) for Gly at position 43 and/or Ala at position of 44, wherein the inserted Cys and any of the substituted Cys form an intramolecular disulfide bond, 2.) Gly substitution for Pro at position 171 in the amino acid sequence of wild type human FGF21 protein; and/or 3) replacement of an amino acid fragment of positions 24 to 31 of the amino acid sequence of wild type human FGF21 protein with an amino acid fragment of 5-15 amino acids, preferably 6-14 amino acids, more preferably 7-13 amino acids, still more preferably 8-10 amino acids, and most preferably 8 amino acids.

In a preferable embodiment, the amino acid fragment for the replacement is a combination of any amino acid.

The abbreviations of the amino acids used herein are as follows:

| Amino acid | 3-letter | 1-letter |
|---|---|---|
| Alanine | Ala | A |
| Arginine | Arg | R |
| Asparagine | Asn | N |
| Aspartic acid | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Proline | Val | V |

In a preferable embodiment, the amino acid fragment for the replacement is a fragment of 8 amino acids, represented by a formula of $X_1X_2X_3X_4X_5X_6X_7X_8$ (SEQ ID NO: 21).

In a preferable embodiment, each of $X_1$-$X_8$ is independently selected from any amino acid, preferably $X_1$ is Ser or Asp, $X_2$ is Gly or Asp, $X_3$ is Pro or Ala, $X_4$ is Ala or Gin, $X_5$ is Gly or Gin, $X_6$ is Leu or Tyr, $X_7$ is Ser or His, and $X_8$ is Ser or Ala.

In an embodiment, based on the spatial structure of FGF21, it has been found that the amino acid P at position 171 of the C-terminus of FGF21 is easily exposed on the surface and is easily degraded by an enzyme, and in the present disclosure, it may be mutated to G, thereby increasing the stability of FGF21, without any influence on the activity of FGF21 (data is not shown). Further, based on the structure, it is found that the space structure of the amino acids at positions 24-31 at N-terminus of FGF21 is a loop, and the length of the loop maintains the activity of FGF21 and has a significant influence on the stability of FGF21. Furthermore, based on the spatial structure of FGF21, it has also been found that in wild-type FGF21, the amino acids at positions 31 and 32 are spatially adjacent to the amino acids at positions 43 and 44, but the structure is not sufficiently stable. After further research, it is unexpectedly discovered that, after inserting a cysteine Cys between positions 31 and 32 without affecting the length of the loop of positions 23-32, the cysteine forms a disulfide bond with the cysteine mutated at position 43 or 44 and stabilizes the structure; in addition, a mutation of the amino acid(s) in the Loop which alters the amino acid constitution of the Loop at positions 24-31 on the basis of the stable structure by the disulfide bond formed between the Cys inserted between positions 31 and 32 and the mutated Cys at position 43 or 44, can sufficiently increase the activity of FGF21. We have resolved the structure of FGF21. From the CD experiment and NMR experiment, it was fully demonstrated that the mutant with the disulfide bond forms a more stable structure. We have compared the activities of wide type FGF21 and the mutant with changed amino acids in the loop, and showed the activity of the mutant FGF21 with a changed loop was significantly higher than that of wide type FGF21 with the original loop.

In an embodiment, when a stable disulfide bond is formed between the Cys added between positions 31-32 and the Cys at position 43 or 44 in the amino acid sequence of the wild-type human FGF21 protein, the length of the amino acid between positions 23-32 in the wild-type FGF21 has an significant influence on the stability of FGF21. Therefore, on the basis of the disclosure of the present description, those skilled in the art can arbitrarily select the length of the fragment and the amino acid species to make further changes or improvements with expectable effects according to the present disclosure.

In a preferable embodiment, the amino acid fragment for the replacement is DDAQQTEA (SEQ ID NO: 19; its corresponding mutant is also referred to as FGF21-AG hereinafter), and the nucleic acid sequence encoding the mutant is set forth in SEQ ID NO: 3, and its amino acid sequence is set forth in SEQ TD NO: 4.

In another preferable embodiment, the amino acid fragment for said replacement is SGPHGLSS (SEQ ID NO: 20; its corresponding mutant is also referred to as FGF21-LG hereinafter), and the nucleic acid sequence encoding the mutant is set forth in SEQ ID NO: 5, and its amino acid sequence is set forth in SEQ ID NO: 6.

In the present disclosure, "wild-type FGF21" is obtainable by searching FGF21 from uniprot.org, and then selecting an organism as Homo sapiens from the obtained results. The human FGF21 is numbered as Q9NSA1 in uniprot, and the protein sequence of our resulting FGF21 has 209 residues. After deleting a signal peptide of the 28 amino acid at its N-terminus, and the resulting FGF21 sequence has 181 residues, which is the wild type FGF21 sequence, whose nucleic acid sequence is SEQ ID NO: 2, and the corresponding amino acid sequence is SEQ ID NO: 1.

Therefore, the "wild type human FGF21 protein" described in the present disclosure refers to a mature FGF21 protein naturally present in humans (hereinafter also referred to as FGF21), and in a typical case, its amino acid sequence is set forth in SEQ ID NO: 1, or is an amino acid sequence having 90% or more, 95% or more, preferably 98% or more, more preferably 99% identity to SEQ ID NO: 1.

"% identity", relative to a reference polypeptide sequence, is defined as after an alignment of sequences is performed, and a gap is introduced as necessary to achieve maximum percent sequence identity without considering any conservative substitution as a part of sequence identity, the percentage of the same amino acid residues in the candidate sequence relative to those in the reference polypeptide sequence. Alignment to determine percentage amino acid sequence identity can be achieved in various ways within the skill of the art, for example, using publicly available software such as BLAST, BLAST-2, ALIGN or Megalign (DNASTAR) software. One skilled in the art can determine parameters appropriate for aligning sequences, including any algorithms needed to achieve maximum alignment over the entire length of the compared sequences. However, for the purposes herein, % homology value is generated by using the sequence comparison computer program ALIGN-2. The author of the ALIGN-2 sequence comparison computer program is Genentech, Inc., and the source code has been submitted to the U.S. Copyright Office, Washington D.C., 20559 along with the user documentation, which is registered under U.S. Copyright Registration No. TXU510087. The ALIGN-2 program is publicly available from Genentech, Inc., South San Francisco, Calif., or the program can be compiled from source code. The ALIGN-2 program should be compiled for being used in UNIX operating systems, including digital UNIX V4.0D. All sequence comparison parameters are set by the ALIGN-2 program and do not need to be changed.

In another aspect, the disclosure provides a nucleic acid encoding any of the mutants described above.

The disclosure further provides a vector comprising the nucleic acid described above. In a preferable embodiment, the vector is an expression vector, more preferably a prokaryotic expression vector.

The disclosure further provides a host cell comprising the vector described above.

In a preferable embodiment, the host cell is an E. coli cell.

The present disclosure further provides a method for producing a human FGF21 mutant, comprising operably linking the coding gene of the human FGF21 mutant to the expression vector to obtain a recombinant expression vector; transforming the recombinant expression vector into a host cell; culturing the recombinant host cell, inducing the expression of the recombinant protein, collecting and purifying the expressed protein.

In a preferable embodiment, the method comprises sequentially ligating a SUMO tag gene (6-his tag at the N-terminus of the SUMO tag gene) and a nucleic acid sequence encoding the human FGF21 mutant. The gene is operably linked to the expression vector to obtain a recombinant expression vector; transforming the recombinant expression vector into a host cell, culturing the recombinant host cell, inducing the expression of the recombinant protein, collecting and purifying the expressed protein, digesting the protein with SUMO enzyme, and re-purifying the protein.

The host cell is an E. coli cell.

It is found that for the mutant of the present disclosure, the induction expression condition may be: culturing the cell at 10-37° C., when its $OD_{600}$ reaches 0.2-1.0, adding IPTG with a final concentration of 0.1-1 mM, and inducing expression at 4-37° C. for 2-20 hours. In a more preferable embodiment, said condition may be: culturing the cell at 37° C., when its $OD_{600}$ reaches 0.8, adding IPTG with a final concentration of 1 mM, and inducing expression at 25° C. for 6 hours.

The purification method of the present disclosure is as follows: re-suspending the collected cell with a lysis buffer (20 Mm Tris-HCl 100 Mm NaCl, pH 8.0), performing a cell lysis, centrifuging and collecting the supernatant, mixing the supernatant with the purified filler, incubating for 0.1-10 hours, transferring the mixture to a chromatography column to purify the protein, digesting the resulting purified SUMO-fused human FGF21 mutant protein with SUMO enzyme, wherein the digestion conditions include: the temperature is 0-37° C., the buffer is 20 Mm Tris-HCl 100 mM NaCl pH 8.0. PBS, Tris-HCl, pH is 6.8-8.0, digestion is performed for 0-24 hours, using Ni metal chelate affinity chromatography to obtain a human FGF21 mutant, and re-purifying the FGF21 mutant protein with size exclusion chromatography.

In another aspect, the disclosure provides the use of the mutant in the manufacture of a medicament for the treatment of type 2 diabetes, obesity, dyslipidemia, or metabolic syndrome.

In another aspect, the disclosure provides a pharmaceutical composition comprising the mutant of the present disclosure and a pharmaceutically acceptable carrier. The term "pharmaceutically acceptable carrier" refers to carriers and auxiliary substances such as diluents or excipients which are compatible with the other ingredients of the formulation. The term "pharmaceutical composition" includes a product comprising a predetermined amount or ratio of a particular ingredient, as well as any product obtained directly or indirectly by combining particular amounts of particular ingredients. Preferably, it comprises a product comprising one or more active ingredients, and optionally a carrier comprising an inert ingredient, as well as any product obtained directly or indirectly from a combination, composition or aggregation of any two or more ingredients, or decomposition of one or more ingredients, or reactions or interactions of other types of one or more ingredients. "Mutation" as used in the present disclosure includes substitution, deletion, and addition of an amino acid.

In summary, the mutant of the present disclosure has more advantages than wild type FGF21. Such advantages include improvement of pharmacological efficacy and/or improvement of drug stability. The FGF21 mutant protein of the disclosure has one or more beneficial physiological characteristics, including a more significant drug efficacy and a greater thermo-stability in vivo. Further, the FGF21 variants of the present disclosure have potential effects in the treatment of type 2 diabetes, obesity, dyslipidemia, or metabolic syndrome, or any of other diseases which can be treated with the FGF21 variant.

EXEMPLARY EMBODIMENTS

Figure 1:
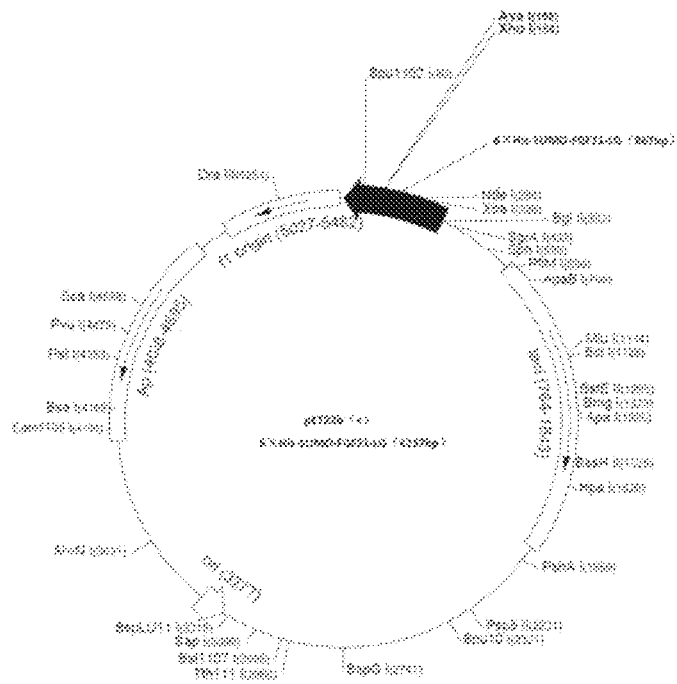
FIG. 1: Schematic representation of the SUMO-FGF21 mutant expression vector.

The invention will be further described in combination with the specific examples, and the advantages and features of the disclosure will become more apparent with the description. However, it will be understood that these examples are merely exemplary, without any limitation to the scope. It should be understood by those skilled in the art that the details and the forms of the present disclosure may be modified or substituted without departing from the spirit and scope of the invention, and the modifications and substitutions still fall within the protection scope of the present disclosure.

The main reagents and instruments used in the experiment of the examples were as follows: the primers used in the cloning were all synthesized by Sangon Biotech (Shanghai) Co. Ltd. In Polymerase Chain Reaction (PCR), DNA polymerase (primer star), restriction endonuclease, ligase, and Dpn I were all purchased from Takara; DNA marker was purchased from Thermo; and Common DNA Product Recovery Kit, and Agarose Gel Recovery Kit were purchased from TIANGEN. E. coli DH5α strain, E. coli BL21 strain, pET22b-SUMO-FGF21 plasmid, and SUMO protease were purchased Beijing Solarbio Science & Technology Co., Ltd. Tris and Imidazole were purchased from Sangon Biotech (Shanghai) Co. Ltd, the other salts were purchased from Sinopharm Chemical Reagent Co., Ltd., and concentration tubes were purchased from Millipore. FPLC instrument used GE's ÄKTA system, and the Ni-Sepharose chromatography column and the molecular exclusion chromatography column Hiload 16/60 Superdex75 pg were purchased from GE. BCA kit was purchased from Thermo.

TABLE 1

Primers used for FGF21 molecular cloning

| Primer name | Primer sequence (5' to 3') |
| --- | --- |
| SUMO-F | GGGAATTCCATATGCATCATCATCATCATCAC (SEQ ID NO: 7)[a] |
| FGF21-R | CCGCTCGAGTCAGGAAGCGTAGCT (SEQ ID NO: 8)[b] |
| SFmid-F | CAGAGAACAGATTGGTGGTCACCCCATCCCTGACTCCA (SEQ ID NO: 9) |
| SFmid-R | TGGAGTCAGGGATGGGGTGACCACCAATCTGTTCTCTG (SEQ ID NO: 10) |
| 171G-F | CATGGTGGGAGGTTCCCAGGGCCGAAG (SEQ ID NO: 11) |
| 171G-R | CTTCGGCCCTGGGAACCTCCCACCATG (SEQ ID NO: 12) |
| 43C-F | GGGACGGTGGGGTGCGCTGCTGACCAG (SEQ ID NO: 13) |
| 43C-R | CTGGTCAGCAGCGCACCCCACCGTCCC (SEQ ID NO: 14) |
| 31-32C-F | CAGCAGACAGAAGCTTGCCACCTGGAGA (SEQ ID NO: 15) |
| 31-32C-R | TCTCCAGGTGGCAAGCTTCTGTCTGCTG (SEQ ID NO: 16) |
| FGF21-LG-F | AGCGGTACCTCTACACATCAGGACCTCATGGGCTCTCAAGTTGCCACCTGGAGATCAG (SEQ ID NO: 17) |
| FGF21-LG-R | CTGATCTCCAGGTGGCAACTTGAGAGCCCATGAGGTCCTGATGTGTAGAGGTACCGCT (SEQ ID NO: 18) |

[a]There are bases for protection at position 1-8, and there are restriction endonuclease sites at positions 9 to 14;
[b]There are bases for protection at positions 1-3 and there are restriction endonuclease sites at positions 4 to 9.

Example 1: Construction of Recombinant FGF21 Mutant Expression Vector

The first mutation was carried out by using the pET22b-SUMO-FGF21 plasmid as a template: PCR site-directed mutagenesis was carried out using an upstream primer 171G-F and a downstream primer 171G-R. A FGF21-P171G mutant was obtained. The second mutation was carried out by using the FGF21-P171G mutant as a template, 43C-F as an upstream primer and 43C-R as a downstream primer to perform PCR site-directed mutagenesis to obtain a FGF21-G43C-P171G mutant. The third mutation: using the FGF21-P171G mutant as a template, 31-32C-F as an upstream primer and 31-32C-R as a downstream primer to perform PCR site-directed mutagenesis to obtain a FGF21-AG mutant. The fourth mutation: using the FGF21-AG as a template, FGF21-LG-F as an upstream primer, and FGF21-GR as a downstream primer to perform the mutagenesis. A FGF21-LG mutant was obtained. The PCR reaction conditions were as follows. The PCR reaction system and reaction procedure of the above mutagenesis process were as follows:

PCR reaction system: 2×Prime STAR HS (Premix) 25 μl, upstream primer (10 μM) 1 μl, downstream primer (10 μM) 1 μl, template 1 μl, ddH$_2$O 22 μl, total volume 50 μl.

PCR reaction procedure: step 1, pre-denaturation temperature 98° C. 10 nuns; step 2, denaturation temperature 98° C. 10 secs; step 3, annealing temperature 57° C. 5 secs; step 4, extension temperature 72° C., 1 min. steps 2 to 4 were repeated for 30 cycles.

Figure 2:
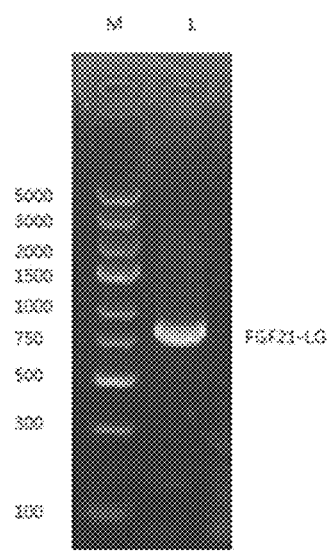
FIG. 2: Electrophoresis pattern of SUMO-FGF21-LG nucleic acid after purification, M represents a DL5000 DNA Marker, and 1 represents a purified product of SUMO-FGF21-LG gene.
Figure 3:
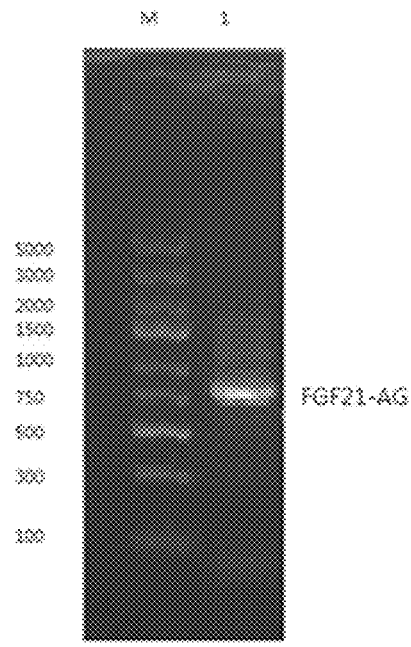
FIG. 3: Electrophoresis pattern of SUMO-FGF21-AG nucleic after purification, M represents a DL5000 DNA Marker, and 1 represents a purified product of SUMO-FGF21-AG gene.

The product resulted from each mutagenesis was digested with Dpn I enzyme for 1 h at 37° C. The digested product was subjected to agarose gel electrophoresis, and the plasmid was recovered by a Gel Recovery Kit. 1 ul plasmid was placed into 100 ul of competent cells, and the cells were placed on ice for 30 minutes, heat-activated at 42° C. for 90 seconds, then added in 400 ul LB, incubated at 37° C. for 45 minutes of shake cultivation, then plated, and inverted at 37° C. overnight. The monoclonal antibody was picked out as a template, and SUMO-F was used as an upstream primer and FGF21-R was used as a downstream primer for PCR identification, wherein the identification results of FGF21-LG are shown in FIG. 2, and the identification structure of FGF21-AG is shown in FIG. 3, The preliminarily, successfully identified FGF21 mutant was subjected to gene sequencing and results analysis. The samples were sequenced by Sangon Biotech (Shanghai) Co. Ltd. Sequence analysis was performed using DNAMAN software. The result of the sequence identification: the nucleic acid sequence of the mutant FGF21-AG is set forth in SEQ ID NO. 3, its corresponding amino acid sequence is set forth in SEQ ID NO. 4; the nucleic acid sequence of the mutant FGF21-LG is set forth in SEQ ID NO. 5, its corresponding amino acid sequence is set forth in SEQ ID NO. 6. A schematic diagram of its construction vector is shown in FIG. 1.

The successfully sequenced plasmid containing the nucleic acid sequence encoding the FGF21 mutant was transformed into the BL21 DE3) strain, the monoclonal strain was picked out for expansion culture, and the strain was stored in a −80° C. refrigerator.

Example 2: Expression of Human Recombinant FGF21 Mutant

The FGF21 mutant strain was seeded into 5 ml LB medium (containing 100 μg/ml ampicillin) at a 2% inculation amount, and cultured overnight with shaking at 37° C. and 220 rpm, and the overnight culture bacteria solution was seeded into each bottle at 2% inculation amount, wherein each 2000 ml triangular bottle contained 500 ml LB medium (containing 100 μg/ml ampicillin), When the OD$_{600}$ was 0.8, 1.0 M IPTG 500 ul was added, and expression was induced at 25° C. for 4 hours. The induced bacteria was centrifuged at 4° C., 8000 r/min for 10 minutes, the supernatant was discarded, and the thallus was collected, and then stored at −80° C.

Figure 4:
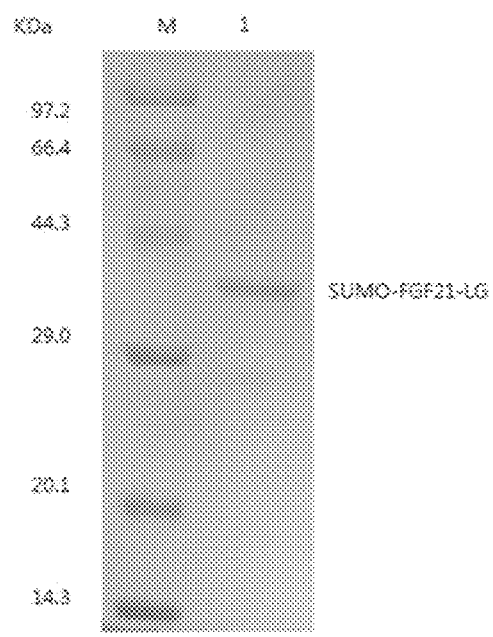
FIG. 4: SDS-PAGE of pET22b (DE3) SUMO-FGF21-LG protein after purification.

Example 3: Purification of Recombinant Human FGF21 Mutant (1) Primary Purification of Recombinant Human FGF21 Mutant The bacteria obtained by expression were resuspended in lysis buffer (50 mM Tris, 300 mM NaCl, pH 8.5), and then lysed by sonication (30% power, sonication for 2 seconds, stop for 5 seconds, total time 45 minutes), then centrifuged at 4° C., 14000 rpm and the supernatant was collected. The supernatant was added to a Ni-Sepharose column that had been pre-equilibrated with buffer, and was mixed in a manner of spin at 4° C. for 30 minutes. After the solution was flowed-through, the column was washed with 5-fold column volumes of buffer to remove unbound protein and impurities, then washed with 5-fold column volume of buffer containing 30 mM imidazole (50 mM Tris, 300 mM NaCl, pH 8.5) to elute non-specific hybrid proteins, then washed with 5-fold column volumes of buffer containing 300 mM imidazole (50 mM Tris, 300 mil NaCl, pH 8.5) to elute the target protein, and the purification result was detected by SDS-PAGE (results see FIG. 4).

(2) Recombinant Human FGF21 Mutant Digestion and Purification

Figure 5:
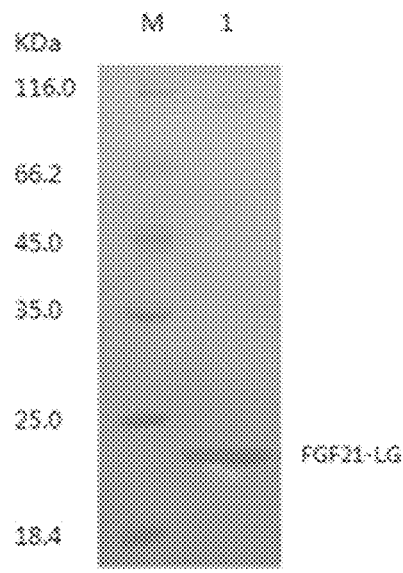
FIG. 5: SDS-PAGE of FGF21-LG protein after purification, M represents a protein molecular weight standard, and 1 represents FGF21-LG.
Figure 6:
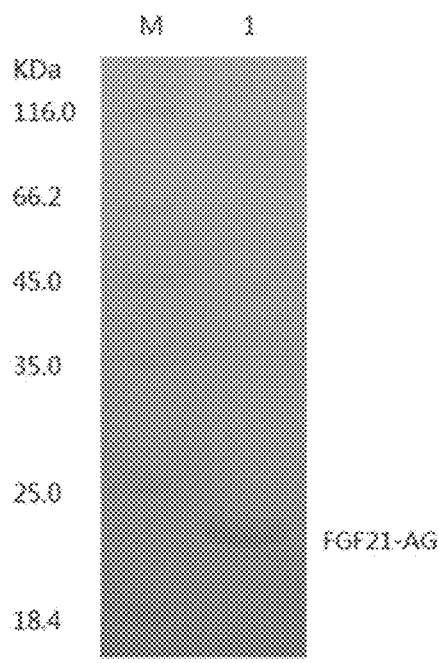
FIG. 6: SDS-PAGE of FGF21-AG protein after purification, M represents a protein molecular weight standard, and 1 represents FGF21-AG.

Detection of the fusion protein: SUMO enzyme was added in a molar ratio of 0.1%, the protein was digested at 4° C. for 2 hours, a final concentration of 20 mM imidazole was added to the digested protein solution, and then the digested protein solution was added into a Ni-Sepharose column pre-equilibrated with a buffer (50 mM Tris, 300 mM NaCl, pH 8.5), and mixed in a manner of spin at 4° C. for 30 minutes. The flow-through solution was collected, concentrated to 10 mg/ml with a concentrating tube, and then purified by Superdex. 75 molecular exclusion chromatography column, wherein the used molecular exclusion chromatography buffer contained 20 mM PBS, 100 mM NaCl pH7.2. The resulting protein was a FGF21 mutant protein, and FGF21 and mutants such as FGF21-LG and FGF21-AG proteins in the experiments were all purified by the above method. And the proteins were detected by 12% SDS-PAGE gel electrophoresis, wherein its result for FGF21-LG protein is shown in FIG. 5, and its result for FGF21-AG protein is shown in FIG. 6.

Example 4: Lowering Blood Glucose by the FGF21 Mutants

Figure 7:
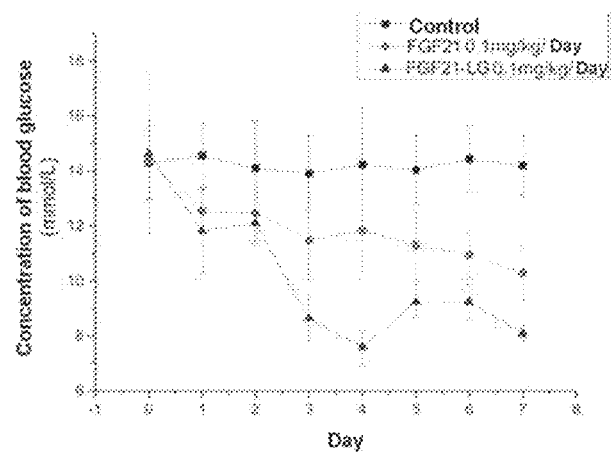
FIG. 7: The result of the FGF21-LG protein drug efficacy experiment in an animal (reducing blood glucose).
Figure 8:
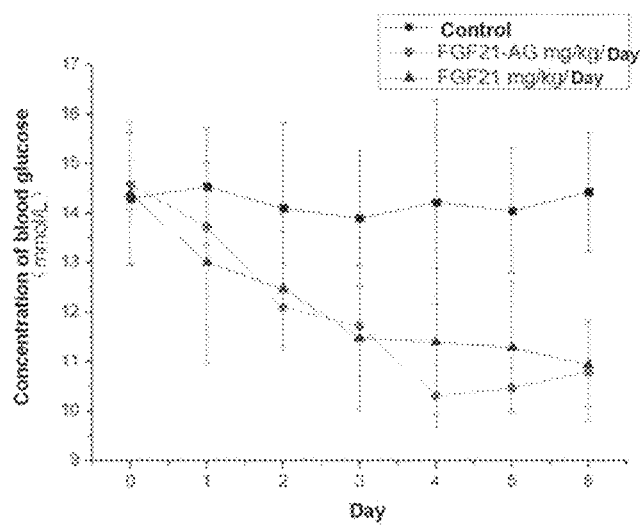
FIG. 8: The result of the FGF21-AG protein drug efficacy experiment in an animal (reducing blood glucose).

Animal experiments were performed using mutant proteins to lower blood glucose. The ob/ob mice (purchased from Model Animal Research Center Of Nanjing University) models were divided into 3 groups (each group 8 rats), which were the vehicle control group (i.e., injected with normal saline), FGF21 group and FGF21-LG group. The administration manner was subcutaneous injection in the back at 0.1 mg/kg/day, by continuous administration for seven days. The blood glucose level was recorded before daily administration. As shown in FIG. 7, the FGF21-LG (FIG. 7) group showed more potent drug efficacy than wild type FGF21 protein. Similarly, the same experiment was carried out for FGF21-AG, the administration manner was at 0.6 mg/kg/day, and the blood glucose level was recorded before daily administration. The experiment shows that FGF21-AG also has an obvious effect to lower blood glucose, and the results are shown ire FIG. 8.

Example 5: Body Weight Loss Experiment of FGF21 Mutant

Figure 9:
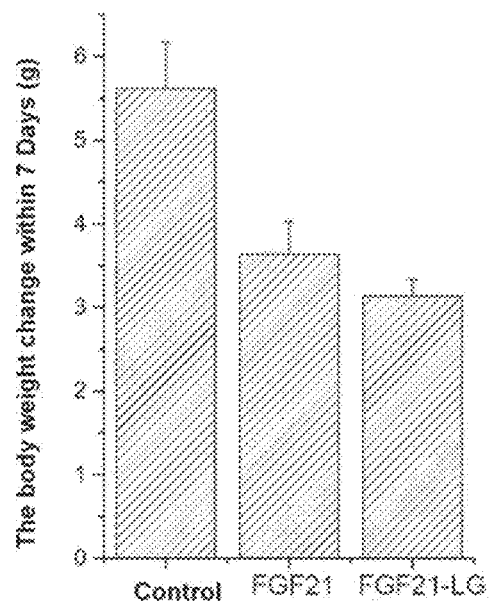
FIG. 9: The result of the FGF21-LG protein drug efficacy experiment in an animal (influence on body weight).
Figure 10:
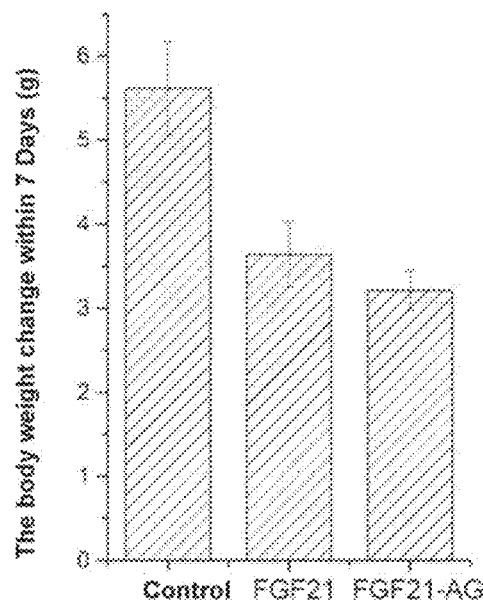
FIG. 10: The result of the FGF21-AG protein drug efficacy experiment in an animal (influence on body weight).

The body weight loss experiment of the animals was carried out with the FGF21 mutant protein. The ob/ob mice were divided into 4 groups, namely, vehicle control group, i.e., injected with normal saline, FGF21 group, human FGF21-LG group, and FGF21-AG group, 8 mice in each group. The purified protein was administered at 0.6 mg/kg/day for 6 consecutive days, and the body weight change was recorded after 6 days. The experiment confirmed that the FGF21-LG (FIG. 9) and FGF21-AG (FIG. 10) groups as compared with the wild-type FGF21 protein has more pronounced weight-losing effect and is more potent drug efficacy.

Example 6: Thermal Stability Test

Figure 11:
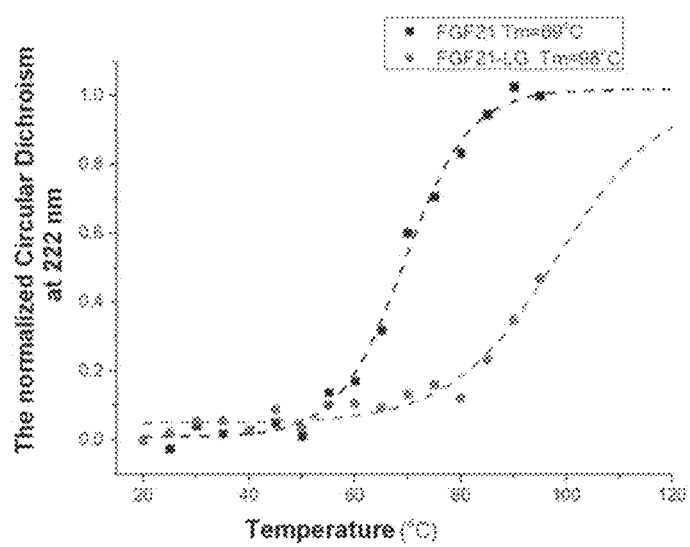
FIG. 11: Thermal stability experiment of FGF21-LG protein.

Experiments were performed using human FGF21 mutants. FGF21 and FGF21-LG were subjected to a temperature-changing experiment using Circular Dichroism (CD) at 20-95° C., and tested at every 5° C. as a test point. The test results showed that the conversion temperature of FGF21 was 69° C., and the conversion temperature of FGF21-LG was 98° C. The experiment proved that human FGF21-LG has better thermal stability than wild type FGF21 (FIG. 11). Similarly, FCD21-AG was used to obtain a similar CD result.

It can be seen that the mutants according to the present disclosure have a better thermal stability than that of the wild type.

The invention claimed is:

1. A human FGF21 mutant, wherein the amino acid sequence of the mutant is set forth in SEQ ID NO: 4.

2. A pharmaceutical composition comprising the mutant of claim 1.

* * * * *